US 6,770,089 B1

(12) United States Patent
Hong et al.

(10) Patent No.: US 6,770,089 B1
(45) Date of Patent: *Aug. 3, 2004

(54) HYBRID STENT FABRICATION USING METAL RINGS AND POLYMERIC LINKS

(75) Inventors: James Hong, San Jose, CA (US); Timothy A. Limon, Cupertino, CA (US); Stephen D. Pacetti, San Jose, CA (US); Rahul Bhagat, San Jose, CA (US); Sharon Segvich, Crown Point, IN (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 172 days.

This patent is subject to a terminal disclaimer.

(21) Appl. No.: 10/032,939

(22) Filed: Dec. 26, 2001

Related U.S. Application Data

(63) Continuation-in-part of application No. 09/753,232, filed on Dec. 28, 2000, now Pat. No. 6,565,599.

(51) Int. Cl.$^7$ .................................................. A61F 2/06
(52) U.S. Cl. ...................................... 623/1.16; 623/1.15
(58) Field of Search ................ 623/1.13–1.2, 623/1.22, 1.27, 1.35, 1.23, 1.3, 1.31, 1.32

(56) References Cited

U.S. PATENT DOCUMENTS

| | | | |
|---|---|---|---|
| 3,868,956 A | 3/1975 | Alfidi et al. | |
| 4,512,338 A | 4/1985 | Balko et al. | |
| 4,553,545 A | 11/1985 | Maass et al. | |
| 4,733,665 A | 3/1988 | Palmaz | |
| 4,762,128 A | 8/1988 | Rosenbluth | |
| 4,800,882 A | 1/1989 | Gianturco | |
| 4,856,516 A | 8/1989 | Hillstead | |
| 4,886,062 A | 12/1989 | Wiktor | |
| 5,591,224 A | 1/1997 | Schwartz et al. | |
| 5,653,727 A | 8/1997 | Wiktor | |
| 5,843,158 A | * 12/1998 | Lenker et al. | 623/1.13 |
| 6,066,167 A | 5/2000 | Lau et al. | |
| 6,143,022 A | 11/2000 | Shull et al. | |
| 6,165,210 A | * 12/2000 | Lau et al. | 623/1.12 |
| 6,315,788 B1 | 11/2001 | Roby | |
| 6,338,740 B1 | 1/2002 | Carpentier | |
| 6,387,122 B1 | * 5/2002 | Cragg | 623/1.16 |
| 6,565,599 B1 | * 5/2003 | Hong et al. | 623/1.15 |

FOREIGN PATENT DOCUMENTS

| | | |
|---|---|---|
| DE | 197 28 337 A1 | 1/1999 |
| WO | WO 98/20810 | 5/1998 |

OTHER PUBLICATIONS

International application published under PCT as Publication No. WO 01/01888A1 to SciMed Life Systems, Inc. (Jan. 11, 2001).

* cited by examiner

Primary Examiner—Corrine McDermott
Assistant Examiner—Hieu Phan
(74) Attorney, Agent, or Firm—Fulwider Patton Lee & Utecht, LLP

(57) ABSTRACT

An expandable hybrid stent having metallic rings and polymer interconnecting links is disclosed. One embodiment of the stent has radially expandable cylindrical rings generally aligned on a common axis and interconnected by one or more polymer links that attach at formations formed in the rings. The polymer links have sufficient column strength to keep the rings from collapsing together axially. The formations may be holes, notches, grooves, channels, dovetails, or the like and the links wrap around, pass through, or lie on the formations. The junction of the link and ring at the formation is then melted and allowed to solidify. Alternatively, beads may be formed on either side of where the link passes through a hole in the ring thus securing the ring to the link.

37 Claims, 4 Drawing Sheets

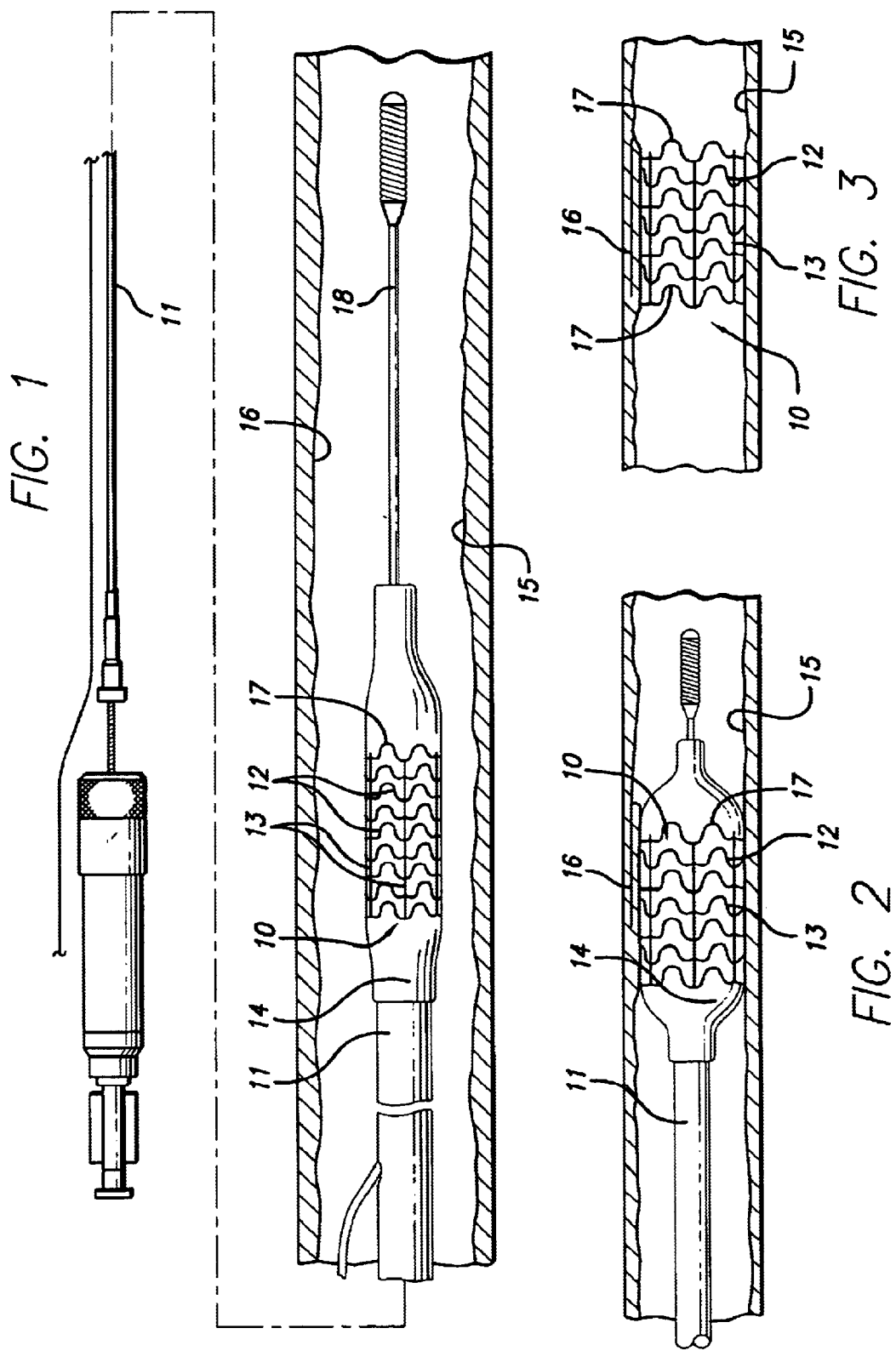

HYBRID STENT FABRICATION USING METAL RINGS AND POLYMERIC LINKS

CROSS-REFERENCE TO RELATED APPLICATIONS

This application is a continuation-in-part of U.S. application Ser. No. 09/753,232, filed Dec. 28, 2000, now U.S. Pat. No. 6,565,599 for a "Hybrid Stent," the entire contents of which are hereby incorporated by reference.

BACKGROUND OF THE INVENTION

The present invention relates to expandable endoprosthesis devices, generally called stents, which are adapted to be implanted into a patient's body lumen, such as blood vessel, to maintain the patency thereof. These devices are useful in the treatment of atherosclerotic stenosis in blood vessels.

Stents are generally tubular-shaped devices which function to hold open a segment of a blood vessel, coronary artery, or other anatomical lumen. They are particularly suitable for use to support and hold back a dissected arterial lining which can occlude the fluid passageway therethrough.

Further details of prior art stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); U.S. Pat. No. 4,886,062 (Wiktor); U.S. Pat. No. 6,066,167 (Lau et al.); and U.S. Pat. No. B1 5,421,955 (Lau et al.), which are incorporated herein in their entirety by reference thereto.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior stents involved maintaining the radial rigidity needed to hold open a body lumen while at the same time maintaining the longitudinal flexibility of the stent to facilitate its delivery. Once the stent is mounted on the balloon portion of the catheter, it is often delivered through tortuous vessels, including tortuous coronary arteries. The stent must have numerous properties and characteristics, including a high degree of flexibility in order to appropriately navigate the tortuous coronary arteries. This flexibility must be balanced against other features including radial strength once the stent has been expanded and implanted in the artery. While other numerous prior art stents have had sufficient radial strength to hold open and maintain the patency of a coronary artery, they have lacked the flexibility required to easily navigate tortuous vessels without damaging the vessels during delivery.

Generally speaking, most prior art intravascular stents are formed from a metal such as stainless steel, which is balloon expandable and plastically deforms upon expansion to hold open a vessel. The component parts of these types of stents typically are all formed of the same type of metal, i.e., stainless steel. Other types of prior art stents may be formed from a polymer, but again, all of the component parts are formed from the same polymer material. These types of stents, the ones formed from a metal and the ones formed from a polymer, each have advantages and disadvantages.

One of the advantages of the metallic stents is their high radial strength once expanded and implanted in the vessel. A disadvantage may be that the metallic stent lacks flexibility which is important during the delivery of the stent to the target site. With respect to polymer stents, they may have a tendency to be quite flexible and are advantageous for use during delivery through tortuous vessels. On the other hand, such polymer stents may lack the radial strength necessary to adequately support the lumen once implanted.

What has been needed and heretofore unavailable is a stent that has a high degree of flexibility so that it can be advanced through the tortuous passageways of a patient and can be readily expanded, yet have the mechanical strength to hold open the body lumen into which it expanded. The present invention satisfied this need.

SUMMARY OF THE INVENTION

The present invention in one exemplary embodiment is directed to an intravascular stent comprising a plurality of metallic rings expandable in a radial direction, wherein each of the rings is aligned on a common longitudinal axis, and each of the rings has at least one formation therein; at least one flexible link formed of a polymer having a proximal end and a distal end, with a length that spans at least two rings; and wherein the link has sufficient column strength to axially separate the rings, and wherein the link interconnects the rings at the formations.

As a result, the present invention expandable stent is relatively flexible along its longitudinal axis to facilitate delivery through tortuous body lumens, but is stiff and stable enough radially in an expanded condition to maintain the patency of a body lumen such as an artery when implanted therein. The resulting stent structure is a series of radially expandable cylindrical rings that are spaced longitudinally close enough so that small dissections in the wall of a body lumen may be pressed back into position against the lumenal wall, but not so close as to compromise the longitudinal flexibility of the stent.

The rings are attached to each other by flexible links such that at least one flexible link attaches adjacent rings. If desired, more than one link can be used to attach adjacent rings. At least some of the links are formed from a polymeric material that provides flexibility to the link and allows the stent to more easily bend or flex along its longitudinal axis as the stent navigates through tortuous vessels or coronary arteries. The flexibility of the links is balanced against the links having sufficient column strength to properly orient and separate the rings along the stent longitudinal axis so that the rings do not telescope into each other, collapse longitudinally, or overlap one another. The combination of the flexible rings and flexible links cumulatively provide a stent that is flexible along its length and about its longitudinal axis, yet is still relatively stiff in the radial direction after it has been expanded in order to maintain the patency of a vessel and to resist collapse.

The stent embodying features of the invention can be readily delivered to the desired body lumen, such as a coronary artery (peripheral vessels, bile ducts, etc.), by mounting the stent on an expandable member of a delivery catheter, for example a balloon, and advancing the catheter and stent assembly through the body lumen to the target site. Generally, the stent is compressed or crimped onto the balloon portion of the catheter so that the stent does not move longitudinally relative to the balloon portion of the catheter during delivery through the arteries, and during expansion of the stent at the target site. In a self-expanding embodiment of the present invention stent, the inflation balloon may be omitted. Such self-expanding stents have metallic rings that are made of nickel-titanium or like shape memory alloys.

Stent deliverability and stent flexibility are improved with the present invention hybrid stent. However, one challenge facing the hybrid stent is the potential for vessel injury caused by the strut or link surface presented to the vessel wall. If the polymer links lie on top of the rings or otherwise protrude outwards, the links might contact the vessel wall upon balloon or self-expansion. This expansion creates anon-uniform force against the vessel wall potentially causing neointimal formation. With greater neointimal formation, there is a higher probability of vessel injury. Also, the junction of a polymer link with a metallic ring might present a larger thickness than the rest of the stent, which could lead to greater restenosis at those points.

To address some of the above-mentioned issues, the present invention stent includes formations at the rings to which the polymer links are joined, attached, bonded, or otherwise secured. These formations could be, for example, a hole, a notch, a groove, or the like. The polymer link is threaded through the hole or passes over the notch or groove. Heat can then be applied to melt the polymer link to the ring. It is also possible to partially or fully encapsulate the junction at which the link meets the ring.

Alternatively, the polymer link may be mechanically locked to the ring. This can be accomplished by wrapping the link around the formation and then optionally heating and welding the polymer to the ring. In yet other embodiments, the polymer link can be threaded though a hole in the ring and beads formed in the polymer on either side of the ring by applying beat. The ring is thus locked in between the beads.

By use of the formations in the rings, it is possible to minimize the profile of the junction where the link meets the ring. Accordingly, any potential trauma to the vessel wall brought about by this junction is minimized.

Other features and advantages of the present invention will become more apparent from the following detailed description of the invention when taken in conjunction with the accompanying exemplary drawings.

BRIEF DESCRIPTION OF THE DRAWINGS

FIG. 1 is a side elevational view, partially in section, of a stent embodying features of the present invention which is mounted on a delivery catheter and disposed within a damaged artery.

FIG. 2 is a side elevational view, partially in section, similar to that shown in FIG. 1 wherein the stent is expanded within a damaged artery.

FIG. 3 is a side elevational view, partially in section, depicting the expanded stent within the artery after withdrawal of the delivery catheter.

DETAILED DESCRIPTION OF THE PREFERRED EMBODIMENTS

Figure 4:
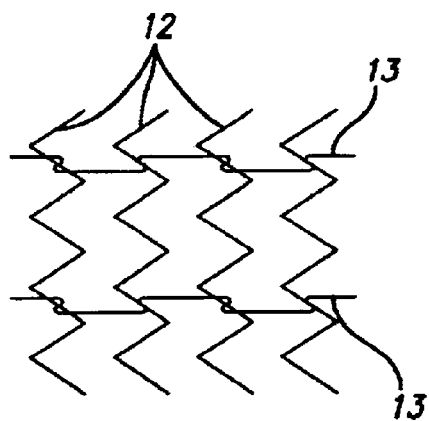
FIG. 4 is a schematic plan view of a flattened section of the present invention stent, illustrating the rings interconnected by the polymer links threaded through the rings.

The present invention is generally directed to a hybrid stent. In one embodiment, a plurality of rings include a metallic material and are interconnected by polymer links to form the stent. FIG. 1 illustrates one embodiment of the stent 10, which stent is mounted on a delivery catheter 11. The stent 10 generally comprises a plurality of radially expandable cylindrical rings 12 that are disposed generally coaxially and are interconnected by links 13 disposed between the adjacent cylindrical rings 12. The delivery catheter 11 has an expandable portion or balloon 14 for expanding of the stent 10 within an artery 15. The artery 15, as shown in FIG. 1, has an occluded portion of the arterial passageway that has been opened by a previous procedure, such as angioplasty.

The delivery catheter 11 onto which the stent 10 is mounted is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 10 to remain in place on the balloon 14 during delivery to the site of the damage within the artery 15, the stent 10 is crimped or compressed onto the balloon in a known manner.

Each radially expandable ring 12 of the stent 10 may be substantially independently expanded to some degree relative to adjacent rings. Therefore, the balloon 14 may be provided with an inflated shape other than cylindrical, e.g., tapered, to facilitate implantation of the stent in a variety of body lumen shapes.

The stent of the present invention may also be self-expanding. In such an embodiment, the rings may be formed from superelastic nickel-titanium (nitinol) and similar alloys. With a self-expanding stent, the balloon may optionally be omitted from the delivery device.

In one embodiment, the delivery of the stent 10 is accomplished in the following manner. The stent is first mounted onto the inflatable balloon 14 on the distal extremity of the delivery catheter by crimping or compressing the stent in a known manner. The catheter-stent assembly is introduced within the patient's vasculature in a conventional Seldinger technique through a guiding catheter (not shown). A guide wire 18 is disposed across the damaged arterial section and then the catheter-stent assembly is advanced over a guide wire 18 within the artery 15 until the stent is positioned at the target site 16. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent 10 in one embodiment from an elongated tube or a flat sheet, the undulating component 17 of the rings 12 of the stent 10 is relatively flat in a cross-section so that when the stent 10 is expanded, the rings 12 are pressed into the wall of the artery and as a result do not interfere with the blood flow through the artery. The rings 12 of the stent 10 which are pressed into the wall of the artery will eventually be covered with endothelial cell growth which further minimizes blood flow interference.

Figure 5:
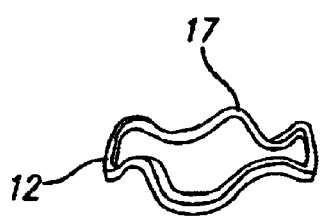
FIG. 5 is a perspective view of an undulating ring.
Figure 6:
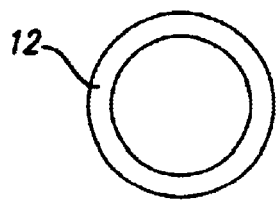
FIG. 6 is a plan view of the undulating ring of FIG. 5.

FIG. 5 illustrates one embodiment of a single corrugated or undulating ring 12 described above, while FIG. 6 illustrates a plan view of the ring 12. The undulating portion 17 of the cylindrical rings provide good tacking characteristics to prevent stent movement within the artery. Furthermore, as seen in FIGS. 1–3, the rings 12 closely spaced at regular intervals provide uniform support for the wall of the artery 15, and consequently are well adapted to tack up and hold in place small flaps or dissections in the wall of the artery 15. Various embodiments for the rings are illustrated in FIGS. 4, 6–7, and 10–13.

FIG. 4 is a partial schematic view of the present invention hybrid stent 10 shown in FIG. 1. In this schematic view, the undulating component 17 and the rings 12 are represented by the vertical jagged lines. The metallic rings 12 are interconnected by polymer links 13 which are represented by the horizontal lines. The point of FIG. 4 is to illustrate the threading, weaving, or winding of the link 13 through formations 19 in the rings 12. The threading, weaving, or winding is represented by the curls in the horizontal line depicting the links 13. Further, each of the links 13 is preferably placed to achieve maximum flexibility for the stent 10.

Figure 7:
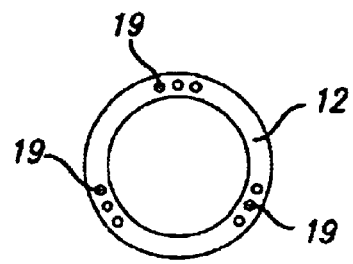
FIG. 7 is plan view of a ring having three sets of three-hole formations.

In the embodiment shown in FIG. 4, the stent 10 has at least three links 13 between adjacent radially expandable cylindrical rings 12, which are spaced 120° apart. As illustrated in FIG. 7, each ring 12 includes formations that help join, secure, fasten the link 13 to the ring 12. In this embodiment, the formations correspond to at least three sets of three holes 19, with each set having at least one link 13 threaded through the holes 19 to connect the link 13 to the ring 12. The rings 12 prior to assembly are held in position by an appropriate fixture such as a mandrel, and the links 13 are threaded and woven through the ring hole clusters 19. The holes 19 may be drilled through the side wall of a pre-made undulating ring with a laser. The holes may also be punched, etched, electrical discharge machined (EDM), or formed through other techniques known in the art.

Once threaded, woven, or secured to the holes 19, the polymer link 13 may be welded to the metallic ring 12 through a variety of processes known in the art. Other techniques for joining the link 13 to the ring 12 are discussed below.

As mentioned above, FIG. 4 illustrates a schematic view of a stent 10 of the present invention wherein three links 13 are disposed between radially expandable rings 12. The links 13 are distributed around the circumference of the stent 10 at a 120° spacing. In various alternative embodiments, the present invention stent may include four or more links 13 between adjacent rings 12. The circumferential spacings between links 13 may be uniform or asymmetric. Also, the links as shown in the FIG. 4 embodiment are generally parallel to the longitudinal axis of the stent, but in various alternative embodiments, the links may be skewed or not parallel to the longitudinal axis or each other.

In an exemplary embodiment, the links 13 are filaments of polymer produced by conventional extrusion methods and having a diameter of about 25–150 microns. The links 13 are extruded from a polymer extruder apparatus 110 shown in FIG. 14 and taken up on a spool. The spool provides a continuous strand of material to form each link for joining the adjacent rings 12 of the stent 10.

Figure 9:
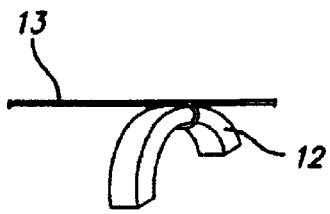
FIG. 9 is a perspective view of a polymer link wrapped 360° around the ring.

This embodiment of the present invention provides a stent wherein the link merges with, or passes through the metal ring, providing a robust joint. The link diameter further provides a hypothetical outer cylindrical plane determined by the longitudinal characteristics of the rings and not the strut pattern or link thickness. The proximal and distal ends of the link each pass through a ring formation and folds back upon itself, wherein the fold back ends of the link are welded to an end ring of the stent. Such a construction is shown in FIG. 9.

Figure 8:
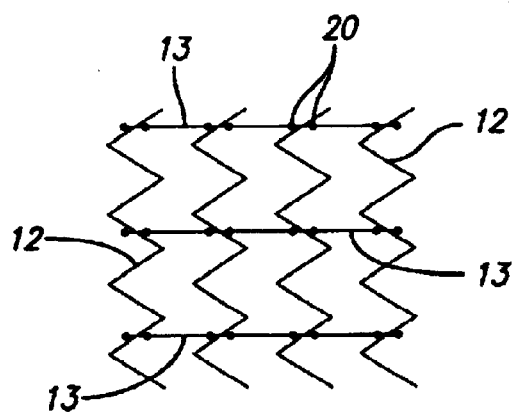
FIG. 8 is a plan view of a flattened section of a stent illustrating the rings secured by links having polymer beads disposed on opposite sides of the ring.

FIG. 8 illustrates another embodiment of the present invention stent. In particular, FIG. 8 is a partial schematic view of a portion of a stent having the links 13 threaded through one of a plurality of single holes formed in the ring, as seen in FIG. 7. In this embodiment, the link 13 is joined, secured, attached, or connected to the ring 12 by forming stops or in this embodiment, beads 20, in the polymer link at opposite sides of each ring 12. The links 13, which are optionally extruded, are passed through the formations or holes 19. The links 13 are next heated proximate to the rings 12 to form the beads 20 on one side of the rings 12. Then the links 13 are heated on the opposite side of the rings 12 to create another group of beads 20. The beads 20 on either side of each ring 20 hold the rings 20 in place. The process is repeated for assembling more rings 12 of the stent together. Selective heating of the link causes just that section of the link to contract and thicken, forming a bead. An IR laser, for example, provides selective heating for the links 13.

In keeping with the invention, the links 13 are formed from a flexible polymer material, or similar material, that is bendable and flexible to enhance longitudinal and flexural flexibility of the stent 10. On the other hand, the polymer should be of sufficient column strength to keep the rings 12 from telescoping or collapsing onto one another.

Figure 10:
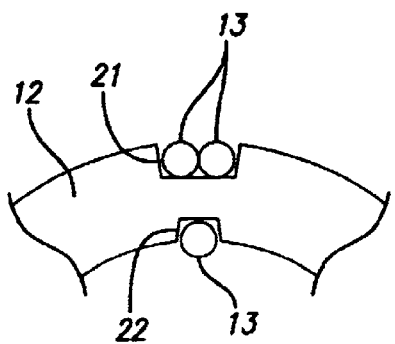
FIG. 10 is a partial end view of the ring-link junction shown in FIG. 9.
Figure 11:
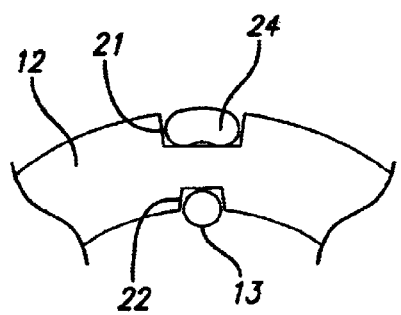
FIG. 11 is a partial end view of the ring-link junction FIG. 10 after the link windings have been fused.

Another embodiment of the present invention provides for mechanically joining the links 13 to the rings 12. This is done by wrapping the link 13 around the ring 12 as illustrated in FIG. 9. FIGS. 10 and 11 further illustrate various embodiments in which the link 13 is wrapped or tied around a formation 22 in the ring 12. After the link 13 completes a 360° turn around the ring 12, the region where the link windings lie side by side are optionally melted 24 by laser welding, thus fusing the windings together as seen in FIG. 11. The link 13 may wrap around or attach to the ring 12 at the formation 22, or at any extension, undulating component, strut, projection, barb, etc., radiating from the basic ring shape.

As further illustrated in FIGS. 10 and 11, the metallic rings 12 have formations 22 cut or otherwise formed in the outer circumference and the inner circumference that allow the links 13 to engage the formations 22. The formations help to precisely locate the junction between the ring and link, to stabilize the windings during assembly or melting, and to minimize movement or slippage of the joint-ring connection. In another embodiment, cement can be laid in the trough-like formations to chemically bond the polymer link to the ring.

In the exemplary embodiment of FIGS. 10–11, the formations are grooves 22 at the inner circumference and notches 21 at the outer circumference. The locations, number, and selection of grooves and notches 22, 21, can be varied according to the link 13 location and other design requirements. For example, the notches or grooves in the outer circumference may be offset from those of the inner circumference to accommodate any pitch in the windings. Their widths may be adjusted as needed to make more or less room for the number of windings. Alternative embodiments of the grooves and notches may have curved, convex or concave walls, a combination of curved and straight walls, a slotted opening, etc.

Figure 12:
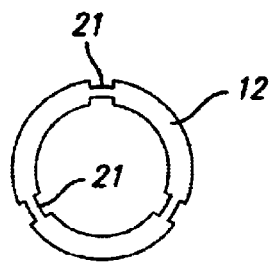
FIG. 12 is an end view of one embodiment of a ring having a notch formation.
Figure 13A:
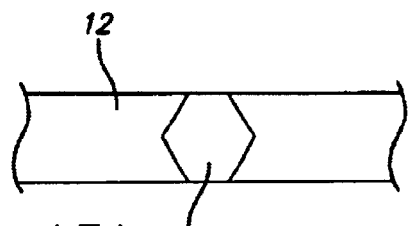
FIGS. 13(*a*) and (*b*) are a partial plan view and end view, respectively, of a keyed notch formation disposed in the outer circumference of a ring.
Figure 13B:
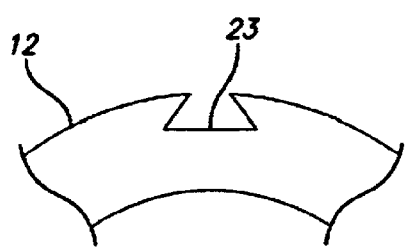

FIG. 12 illustrates another embodiment, wherein a plurality of outer and inner circumference notches 21 only are used on the ring 12. In another alternative embodiment (not shown), the ring includes a polymer molding formed around where the ring 12 and link 13 connect. The polymer molding completely captures the cross-sectional diameter of the ring 12.

The notch and groove formations 21, 22 are made by laser machining, mechanical machining, drawing the ring through a die having notches or grooves, or EDM. As will be further described herein, the polymer used to form the links around the ring formations can be injection molded, as opposed to extruded polymer links.

Another embodiment of the formation is shown in the top plan view and end view of FIGS. 12(a) and (b), respectively. This embodiment contemplates a keyed notch or dove tail formation 23 at the outer circumference of the ring 12. The hexagonal opening of the formation 23 as seen in FIG. 12(a) helps retain a complementary or similarly shaped bead formed in the link 13. The corners in the hexagon of the keyed formation 23 engage the corners of the hexagonal bead, thus preventing relative longitudinal movement between the ring and the link. This arrangement captures the link within the keyed formation 23. Of course, other shapes aside from a hexagon can be formed into the ring to capture the link thus eliminating relative motion. This formation 23 can also be used for fastening links in conjunction with any of the techniques mentioned above.

Figure 15:
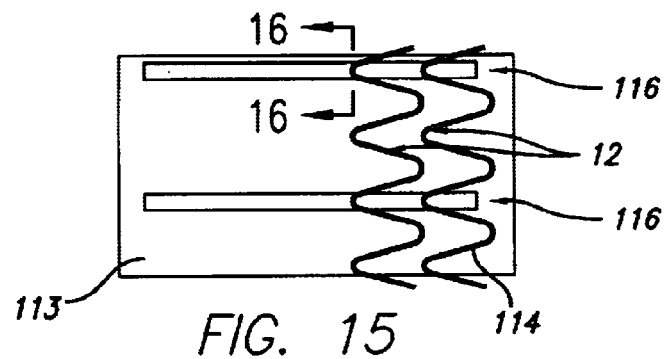
FIG. 15 is a plan view of two rings joined by two extruded polymer links.
Figure 16:
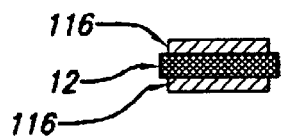
FIG. 16 is a cross-sectional view of one junction of the stent shown in FIG. 15 showing the pre-cut ring encapsulated by the polymer link after the extrusion process.
Figure 17:
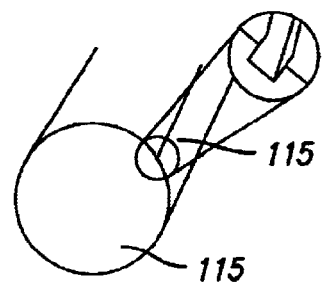
FIG. 17 is a perspective view with an enlarged detailed view of a mandrel having channels wherein a polymer fills the channels to create the polymer links used to join the rings placed on the mandrel.

As previously described, the links of the various embodiments of the invention are formed from a polymer material, then attached in the manner described. With respect to the embodiments depicted in FIGS. 4–13, the links can be fabricated through a polymer-link extrusion process. Any biocompatible thermoplastic polymer can be extruded in any cross-sectional or coating form. The extrusion process can be used to produce continuous polymer links, as described above, or used in conjunction with alternative ring designs or materials to encapsulate both the link 13 and ring 12. This is shown in FIGS. 15–16.

Figure 14:
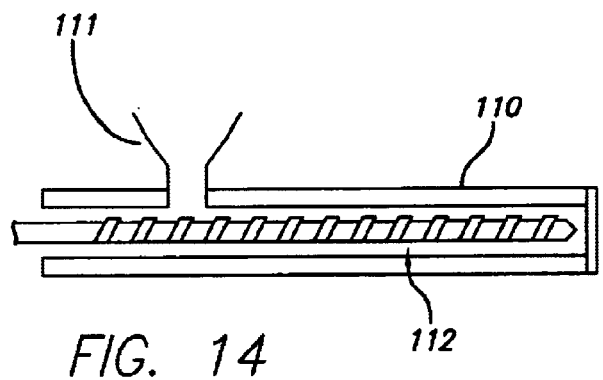
FIG. 14 is schematic view of a polymer extruder apparatus.
Figure 18:
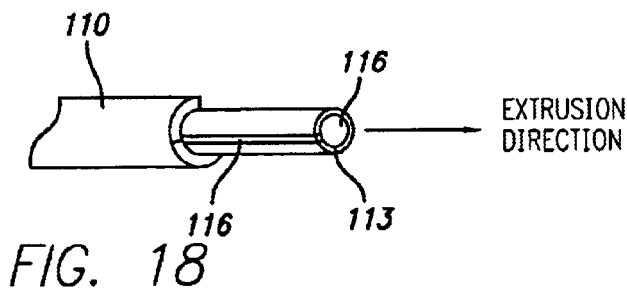
FIG. 18 is a perspective view of the mandrel of FIG. 17 in which polymer links are extruded through a tool.

One method of the present invention for forming the links and attaching them to the rings entails a polymer extrusion apparatus 110 as shown in a schematic depiction in FIG. 14. Biocompatible polymer pellets are fed into a hopper 111 that supplies the pellets to a plasticating single screw extruder 112. A mandrel 113 is provided, as seen in FIGS. 15, with channels 114 that correspond to the strut pattern of the rings 12. The individual rings 12 are placed on the mandrel 113 and fitted into the ring channels 114. The mandrel 113 is fed through the extruder 110, as seen in FIG. 18, where strands of polymer 116 are selectively placed simultaneously at multiple locations around the circumference, and run along the length of the stent.

The mandrel 113 has link channels 115 in which the injected polymer flows. The melted polymer upon cooling joins forms the link as well as the connection between the link and the ring. As illustrated in FIGS. 15–16, the polymer used to form the links optionally encapsulates the metal ring at the polymer/metal contact point.

After the stent and mandrel have a chance to cool so that the polymer solidifies, the stent can be removed from the mandrel 113 and any excess flashing can be removed by processes known in the art. The rings 12 are then removed from the mandrel along with the links 13 resulting in a completed stent 10.

Generally speaking, links 13 can be formed by polymer extrusion according to the methods described herein or by traditional injection molding techniques. Some examples of materials that can be used to form the links include polyurethanes, polyetherurethanes, polyesterurethanes, silicone, thermoplastic elastomer (C-flex), polyether-amide thermoplastic elastomer (PEBAX), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrite, rubber, a family of elastomers composed of styrene, ethylene, propylene, aliphatic polycarbonate polyurethane, polymers augmented with antioxidants, polymers augmented with image enhancing materials (e.g., barium sulfate), polymers having a proton (H+) core, polymers augmented with protons (H+), butadiene and isoprene (Kraton) and polyester thermoplastic elastomer (Hytrel).

Other thermoplastic materials may used for the polymer link, including high molecular weight polyethylene (HMWPE), EVAL, teflon, or FEP. Other thermosets such as polymethylmethacrylate (PMMA) can be used as well. This material has a low percent elongation, but the links in a stent might not require much elongation in certain applications.

Lastly, bioerodable materials or polymers such as EVAL that slowly dissolve in body fluids may be used to make the links. After implantation of the stent, the links slowly dissolve leaving the scaffolding function to the remaining rings.

One method of making the stent 10 of the present invention is to first laser cut the rings 12 from a single tube. The individual rings 12 are then placed on the mandrel 113 into the strut-patterned channels 114 and encased with an optional locking sleeve having a mirror of the strut pattern cut into its inner surface. The only exposed regions of the stent are the channels that correspond to the links that will connect the rings. The mandrel and the encapsulating sleeve permit the injection of a polymer which fills the channels corresponding to the links. The polymer is used to form the links which connect adjacent rings. In accordance with the invention, it is preferred to cut the tubing in the desired pattern using a machine-controlled laser. The polymer links can them be added in a subsequent step. Moreover, the laser cut process can be used after the formation of the polymer links on the metallic rings to trim off excess material or to further produce a desired strut pattern.

The tubing may be made of suitable biocompatible material such as stainless steel, cobalt-chrome (CoCr, MP35N), titanium, nickel-titanium (NiTi), tantalum, platinum, platinum/iridium, Elgiloy, and alloys thereof. The stainless steel tube may be an alloy such as: 316L SS, Special Chemistry per ASTM F138-92 or ASTM F139-92 grade 2, Special Chemistry of type 316L per ASTM F138-92 or ASTM F139-92 Stainless Steel for Surgical Implants in weight percent shown below.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch.

The tubing is put in a rotatable collet fixture of a machine-controlled apparatus for positioning the tubing relative to a laser. According to machine-encoded instructions, the tubing is rotated and moved longitudinally relative to the laser which is also machine-controlled. The laser selectively removes the material from the tubing by ablation and a pattern is cut into the tube. The tube is therefore cut into the discrete pattern of the finished cylindrical rings.

Cutting a fine structure (0.0035 inch web width) requires minimal heat input and the ability to manipulate the tube with precision. It is also necessary to support the tube yet not allow the stent structure to distort during the cutting operation. In one embodiment, the tubes are made of stainless steel with an outside diameter of 0.060 inch to 0.095 inch and a wall thickness of 0.002 inch to 0.004 inch. These tubes are fixtured under a laser and positioned utilizing a CNC to generate a very intricate and precise pattern. Due to the thin wall and the small geometry of the stent pattern (0.0035 inch typical strut or ring width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris free cut, a Q-switched Nd/YAG, typically available from Quantronix of Hauppauge, New York, that is frequency doubled to produce a green beam at 532 nanometers is utilized. Q-switching produces very short pulses (<100 nS) of high peak powers (kilowatts), low energy per pulse ($\leq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure. Hence, the system makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.) The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris block protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inch) with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCL for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCL for 1–4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structures are rinsed in water. They are now ready for electropolishing.

The stent rings are optionally electrochemically polished in an acidic aqueous solution such as a solution of ELECTRO-GLO#300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110–135° F. and the current density is about 0.4 to about 1.5 amps per in.$^2$, Cathode to anode area should be at least about two to one.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal.

The foregoing laser cutting process to form the rings 12 can be used with other metals including cobalt-chrome, titanium, tantalum, nickel-titanium, and other biocompatible metals suitable for use in humans, and typically used for intravascular stents. Further, while the formation of the rings is described in detail, other processes of forming the rings are possible and are known in the art, such as by using chemical etching, electronic discharge machining, stamping, and other processes.

While the invention has been described in connection with certain disclosed embodiments, it is not intended to limit the scope of the invention to the particular forms set forth, but, on the contrary it is intended to cover all such alternatives, modifications, and equivalents as may be included in the spirit and scope of the invention as defined by the appended claims.

What is claimed is:
1. An intravascular stent, comprising:
 a plurality of metallic rings expandable in a radial direction, wherein each of the rings is aligned on a common longitudinal axis;
 each of the rings having at least one formation therein;
 at least one flexible link formed of a polymer having a proximal end and a distal end, and a length that spans at least two rings; and
 wherein the link has sufficient column strength to axially separate the rings, and wherein the link interconnects the rings at the formations.

2. The intravascular stent of claim 1, wherein the formation includes a structure in the ring selected from the group consisting of a hole, a notch, or a groove.

3. The intravascular stent of claim 1, wherein the formation includes a hole in the ring, and wherein the link passes through the hole.

4. The intravascular stent of claim 3, wherein the link includes spaced apart beads positioned on opposite sides of the hole in the ring.

5. The intravascular stent of claim 3, wherein the link passes through the hole and wraps around the ring.

6. The intravascular stent of claim 1, wherein the formation includes at least one of a notch and a groove and the link engages at least one of the notch and the groove.

7. The intravascular stent of claim 1, wherein the metallic rings include a material selected from the group consisting of stainless steel, titanium, tantalum, platinum, platinum-iridium, nickel-titanium, cobalt-chrome, and alloys thereof.

8. The intravascular stent of claim 1, wherein in the polymer material forming the link is selected from the group of polymers consisting of polyurethanes, polyetherurethanes, polyesterurethanes, silicone, thermoplastic elastomer (C-flex), polyether-amide thermoplastic elastomer (PEBAX), fluoroelastomers, fluorosilicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile, rubber, a family of elastomers composed of styrene, ethylene, propylene, aliphatic polycarbonate polyurethane, polymers augmented with antioxidents, polymers augmented with image enhancing materials, polymers having a proton (H+) core, polymers augmented with protons (H+), butadiene and isoprene (Kraton), polyester thermoplastic elastomer (Hytrel), high molecular weight polyethylene (HMWPE), EVAL, teflon, FEP, and polymethylmethacrylate (PMMA).

9. The intravascular stent of claim 1, wherein the link includes a bioerodable material.

10. The intravascular stent of claim 1, wherein the polymer link is extruded on to the ring at the formation.

11. The intravascular stent of claim 1, wherein the rings include a keyed formation interlocked to a complementary shaped bead formed in the link.

12. The intravascular stent of claim 1, wherein the formation of each ring includes at least one set of a plurality of grouped holes, and wherein the link is threaded through the plurality of grouped holes interconnecting the link to the ring.

13. The intravascular stent of claim 1, wherein one of an end of the link passes through the formation and folds back upon itself.

14. The intravascular stent of claim 1, wherein the link includes increased mass that engages the formation.

15. The intravascular stent of claim 1, wherein the formation includes a plurality of single holes that are uniformly spaced apart.

16. The intravascular stent of claim 1, wherein the formation includes a plurality of hole clusters that are spaced symmetrically around the ring.

17. An intravascular stent, comprising:
a plurality of flexible cylindrical rings expandable in a radial direction, each of the rings having a first delivery diameter and a second implanted diameter and aligned on a common longitudinal axis;
wherein some of the rings include a metallic material;
wherein the rings include a formation;
a link formed of a polymer and having a proximal end and a distal end, wherein the link engages the rings at the formation; and
means for affixing the link to the rings.

18. The stent of claim 17, wherein the means for affixing includes wrapping the link around the ring at the formation.

19. The stent of claim 17, wherein the means for affixing includes stops in the link at opposite sides of the formation.

20. The stent of claim 17, wherein the means for affixing includes mechanically interlocking the link to the ring at the formation.

21. The stent of claim 17, wherein the means for affixing includes heating the link to form a first polymeric bead, threading the link through the formation, and heating the link to form a second polymeric bead thereby holding the ring between the beads.

22. The stent of claim 17, wherein the means for affixing includes bonding the link to the formation.

23. An intravascular stent, comprising:
a plurality of metallic rings expandable in a radial direction, wherein the rings are aligned on a common longitudinal axis, and each ring has an outer circumference and an inner circumference;
a plurality of notches disposed at the outer circumference and the inner circumference of the rings; and
a flexible link formed of a polymer, the link having a proximal end and a distal end, and having sufficient column strength to axially separate the rings, wherein the link joins adjacent rings together at the notches.

24. The stent of claim 23, wherein the link at one of the proximal and distal ends is wrapped around the outer circumferential notch and the inner circumferential notch.

25. The stent of claim 23, wherein the link is wound around the ring at the notches, and adjacent windings of the link are fused together.

26. The stent of claim 23, wherein the link and the ring at the notches are at least partially encapsulated in a polymer.

27. The stent of claim 23, wherein the link has a smaller thickness than a thickness of the ring.

28. The stent of claim 23, wherein the ring includes an exterior surface and an interior surface, and the link includes increased mass that engages the notch at one of the exterior surface and the interior surface.

29. The stent of claim 23, wherein the link is tied to the ring at the notch.

30. A method for providing an intravascular stent, comprising:
providing a plurality of metallic rings expandable in a radial direction;
creating a formation on each ring;
aligning the rings along on a common longitudinal axis;
providing at least one flexible link formed of a polymer having sufficient column strength to axially separate the rings, and having a length that spans at least two rings; and
interconnecting the rings with the flexible link at the formations.

31. The method of claim 30, wherein the step of interconnecting the rings includes at least one of welding the link to the ring at the formation, wrapping the link around the ring at the formation, passing the link through the formation, bonding the link to the formation, and at least partially encapsulating the link to the ring at the formation with a polymer.

32. The method of claim 30, wherein the method further comprises:
arranging a plurality of pre-cut rings on a mandrel;
heating polymer pellets into a melt;
extruding the melt; and
guiding the melt over the rings to form the link.

33. The method of claim 30, wherein the method further comprises laser cutting a pattern into the stent.

34. The method of claim 32, wherein the extruded polymer link is spun onto a spool.

35. The method of claim 32, wherein the method further comprises providing a polymer extruder apparatus including a hopper for receiving biocompatible polymer pellets, providing a plasticating single screw extruder, and extruding the polymer to form the link.

36. A method for fabricating a flexible intravascular stent, comprising:
providing a metallic tube;
creating a formation on the tube;
cutting the metallic tube to form a plurality of rings;
arranging the rings on a mandrel;
forming a polymer link by injection molding a polymer onto the plurality of rings; and
encapsulating a junction where the link contacts the formation of the rings thereby interconnecting the rings together.

37. The method of claim 36, wherein the method further comprises at least one of laser cutting, chemically etching, and laser welding the links.

* * * * *